(12) United States Patent
Gopalsami et al.

(10) Patent No.: US 7,495,218 B2
(45) Date of Patent: Feb. 24, 2009

(54) PASSIVE MILLIMETER WAVE SPECTROMETER FOR REMOTE DETECTION OF CHEMICAL PLUMES

(75) Inventors: Nachappa Gopalsami, Argonne, IL (US); Sasan Bakhtiari, Argonne, IL (US); Apostolos C. Raptis, Argonne, IL (US); Thomas W. Elmer, Willowbrook, IL (US)

(73) Assignee: U Chicago Argonne LLC, Chicago, IL (US)

( * ) Notice: Subject to any disclaimer, the term of this patent is extended or adjusted under 35 U.S.C. 154(b) by 304 days.

(21) Appl. No.: 11/407,711

(22) Filed: Apr. 20, 2006

(65) Prior Publication Data

US 2007/0246652 A1    Oct. 25, 2007

(51) Int. Cl.
*G01J 5/00* (2006.01)
(52) U.S. Cl. .................................. 250/336.1
(58) Field of Classification Search ............ 250/336.1, 250/341.1
See application file for complete search history.

(56) References Cited

U.S. PATENT DOCUMENTS

| | | | | |
|---|---|---|---|---|
| 4,415,265 A | * | 11/1983 | Campillo et al. ............ 356/338 |
| 5,468,964 A | * | 11/1995 | Gopalsami et al. ........... 250/393 |
| 5,726,450 A | * | 3/1998 | Peterson et al. ........... 250/338.5 |
| 6,271,522 B1 | * | 8/2001 | Lindermeir et al. ....... 250/341.1 |
| 6,777,684 B1 | * | 8/2004 | Volkov et al. ............. 250/341.1 |
| 6,853,452 B1 | * | 2/2005 | Laufer ......................... 356/436 |
| 6,885,965 B2 | * | 4/2005 | Butler et al. ................. 702/130 |
| 2002/0166969 A1 | * | 11/2002 | Chou et al. ............. 250/339.08 |
| 2004/0211900 A1 | * | 10/2004 | Johnson .................... 250/338.5 |
| 2005/0056785 A1 | * | 3/2005 | Chou et al. .............. 250/338.1 |
| 2007/0090824 A1 | * | 4/2007 | Ammar ................... 324/76.14 |
| 2007/0263682 A1 | * | 11/2007 | Zhang et al. .................. 372/25 |

\* cited by examiner

*Primary Examiner*—David P Porta
*Assistant Examiner*—Marcus H Taningco
(74) *Attorney, Agent, or Firm*—Foley & Lardner LLP

(57) ABSTRACT

Systems and methods for the passive measurement of spectral lines from the absorption or emission by polar molecules. The system includes mmW front-end assembly, back-end electronics, and data acquisition hardware and software was assembled. The method relates to methods for processing multi-channel radiometric data from passive mmW detection systems.

9 Claims, 16 Drawing Sheets

PASSIVE MILLIMETER WAVE SPECTROMETER FOR REMOTE DETECTION OF CHEMICAL PLUMES

The United States Government has rights in this invention pursuant to Contract No. W-31-109-ENG-38 between the United States Government and Argonne National Laboratory.

BACKGROUND OF THE INVENTION

The present invention relates generally to the field of remote detection. Specifically, the present invention relates to passive millimeter wave spectroscopy for remote detection.

Remote detection systems have become increasingly important in helping to regulate behavior of individuals and corporations. Remote sensing devices serve a wide range of functions from detecting contamination to determining if a person is carrying contraband. Some situations require that a remote sensing device be able to function over a large distance rather than over a short-range only.

Active and passive spectrometers operating in the optical range have been employed in the past for a variety of environmental monitoring applications. Optical techniques are commonly used for remote sensing. However, optical systems, which provide superb sensitivity as a direct consequence of high-energy vibrational transitions, are limited in their scope of application because of their extreme sensitivity to atmospheric effects and inherent range limitations. Remote sensing of terrestrial targets based on radar backscattering at microwave frequencies are routinely used to monitor temporal variations of the earth's surface. Short-range spectroscopic measurement of molecular absorptions at millimeter wave frequencies have also been studied extensively in the past, primarily as laboratory-based techniques. Passive microwave sensing and imaging of materials have also been applied in the past for special applications, including the measurement of thicknesses for dielectric medium and short-range determination of thermal and chemical signatures.

Because of the thermal interaction at atomic and molecular level, all materials radiate electromagnetic (EM) energy. A radiometer, which essentially is a highly sensitive receiver, can be used to detect blackbody radiation over a narrow range of the EM spectrum. With the radiation spectrum being governed by Planck's radiation law, the sensor output is a measure of the temperature of the scene; it varies nearly linearly at millimeter wavelengths. Passive sensing of EM radiation at microwave frequencies has been used in the past primarily for radioastronomical and atmospheric observations for which the sensor antenna is directed away from the surface of the earth.

Radio frequency (RF) radiometers are generally designed to operate within atmospheric windows in the microwave and low millimeter-wave (MMW) bands where attenuation due to highly absorbing molecules in the atmosphere is lower. Millimeter waves are radio waves sent at terahertz frequencies, known as terahertz radiation, terahertz waves, T-rays, T-light, T-lux and THz, are in the region of the light spectrum between 10 terahertz and 100 gigahertz, corresponding to the wavelength range 30 micrometers (ending edge of far-infrared light, micrometer wavelength) to 3 mm (starting edge of microwave radiation, millimeter wavelength).

The primary application of passive MMW remote sensing has so far been dedicated to satellite and high-altitude observation of the upper atmosphere. However, there is a need for application of spectroscopic techniques for passive terrestrial detection of target molecules in a chemical plume at millimeter wave frequencies.

SUMMARY OF THE INVENTION

One aspect of the invention relates to a system for passive measurement of spectral lines from the absorption or emission by polar molecules. The system includes mmW front-end assembly, back-end electronics, and data acquisition hardware and software. Another aspect of the present invention relates to methods for processing multi-channel radiometric data from passive mmW detection systems. In one embodiment, amplitude is normalized; the frequency domain scene is subtracted; the time domain is integrated; the time domain baseline is subtracted out; and the channels are stacked. Another aspect of the present invention relates to the application of mmW radiometric techniques for the terrestrial remote sensing of chemical plumes.

These and other objects, advantages, and features of the invention, together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

FIG. 5A illustrates results where cloud temperature is relatively high ($T_c$: 350 K) and where $\theta=85$; $R_c\sim1.15$ km; $R_{bg}\sim5.7$ km; $H_c$: 0.1 km; $D_c$: 0.01 km; V%NO: 1 and FIG. 5B illustrates results where cloud temperature is lower relative to FIG. 5A ($T_c$: 288.15K) and where $\theta=85$; $R_c\sim1.15$ km; $R_{bg}\sim5.7$ km; Tc: 288.15 K; $H_c$: 0.1 km; $D_c$: 0.01 km; V%NO: 1;

FIG. 14A depicts the difference between the sum of middle channels where the signal is high and the sum of outer channels where the signal is flattening, with the inset showing the plume concentration as a function of time, measured by a stack-mounted FTIR instrument; FIG. 14B depicts relative signal levels of all channels at the time of NO release, along with a curve fit that matches the NO spectrum and during hot air alone.

DETAILED DESCRIPTION OF THE PREFERRED EMBODIMENTS

Radiometric sensors do not transmit any electromagnetic radiation making them particularly suited for a wide range of remote sensing applications in which passive sensing is the primary requirement. Furthermore, as a direct consequence of operating at longer wavelengths, millimeter waves penetrate/originate from deeper into material media and are more immune to atmospheric effects in comparison to their optical counterparts.

The present invention relates to systems and methods to remotely detect specific effluent chemicals, such as from material processing plants, using passive millimeter-wave spectroscopic technique. In one embodiment, the present invention allows for the detection of molecular species inside a plume and at large standoff distances using high-frequency millimeter waves. Because the present invention is passive, no signal is transmitted toward the target. Passive sensing is particularly attractive for a wide range of applications that include environmental compliance and arms control treaty verification. Furthermore, as a direct consequence of operation at longer wavelengths in comparison to optical techniques the present invention is less susceptible to harsh atmospheric conditions and can be operated from larger standoff distances to the target.

Figure 1:
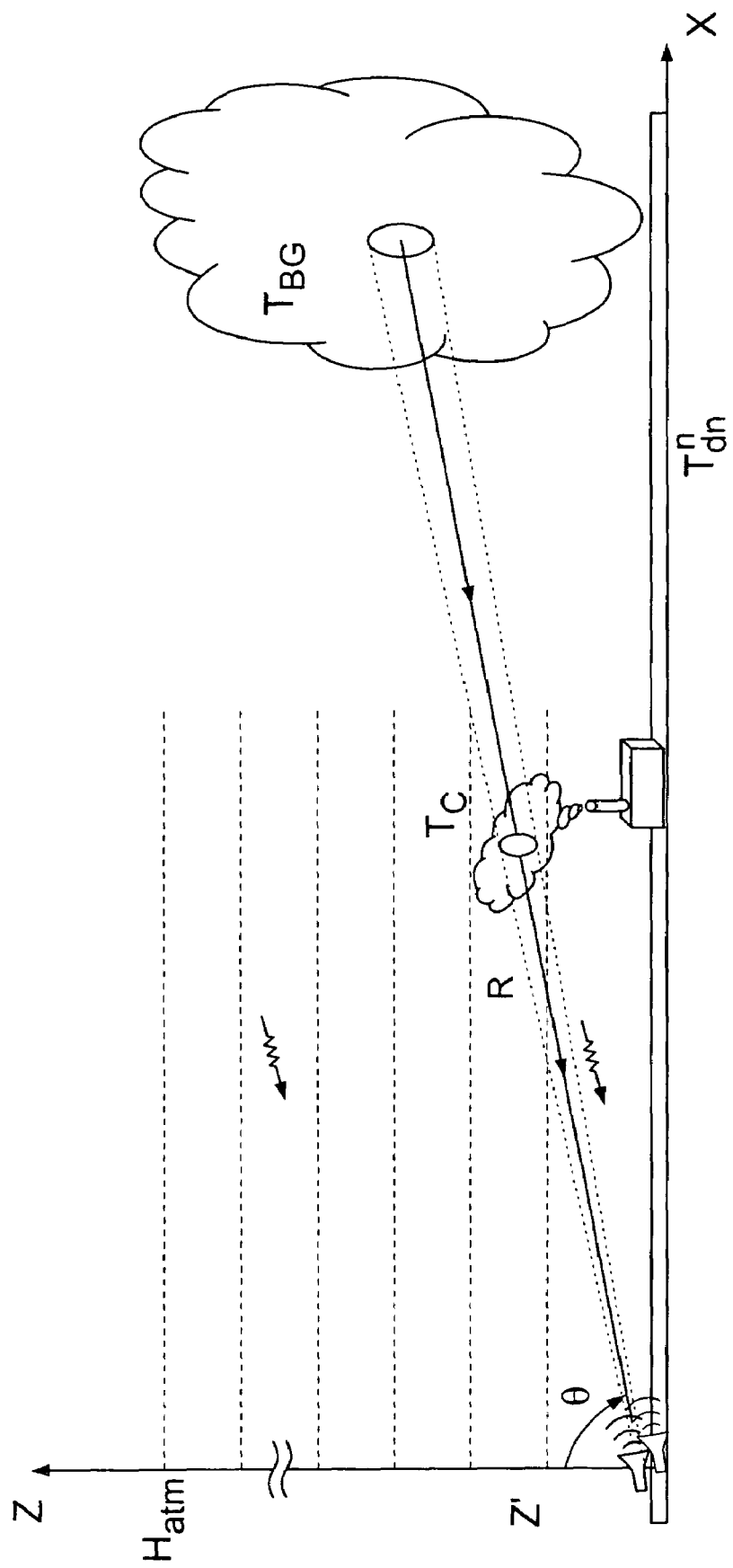
FIG. 1 illustrates, for one embodiment, exemplary geometry of the radiative transfer model consisting of gas plume and background within a stratified atmosphere wherein $T_{dn}$ is the down-welling radiation, $\theta$ is the zenith angle, $R_c$ is the distance to the cloud, and $H_{atm}$ is the height of the atmosphere.

FIG. 1 illustrates, for one embodiment, exemplary geometry of the radiative transfer model 108 consisting of gas plume 101 and background 103 within a stratified atmosphere wherein T$_{dn}$ is the down-welling radiation 105, θ is the zenith angle 109, R$_c$ is the distance to the cloud or plume 101, and H$_{atm}$ is the height of the atmosphere. The radiative transfer equation is used to model the down welling radiation from the plume 101, atmosphere, 108 and background 103.

Figure 2:
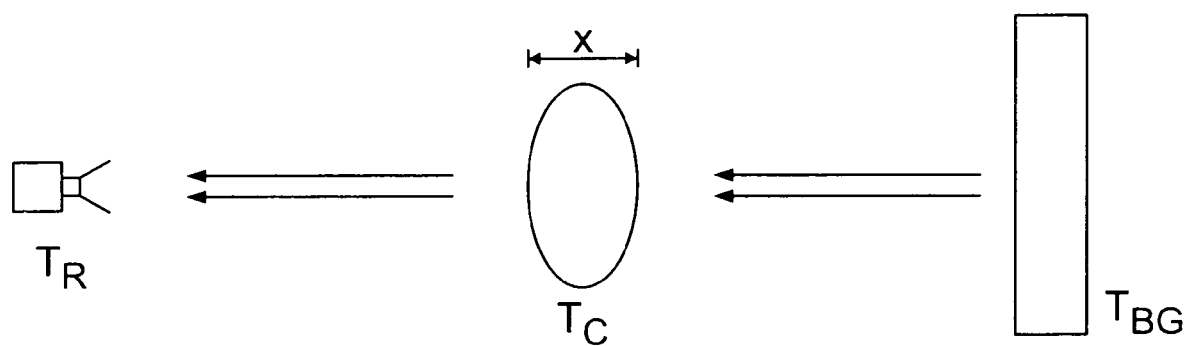
FIG. 2 illustrates of the physics of a passive mmW detector where $T_r$ is the brightness temperature of the scene, $T_c$ is the temperature of the cloud and $T_{bg}$ is the temperature of the background.

FIG. 2 is a graphic illustrating the physics of a passive mmW detector. T$_r$ is the temperature of the reference, T$_c$ is the temperature of the cloud and T$_{bg}$ is the $$B_f(T) \cong \frac{2kT}{\lambda^2}$$

temperature of the background. The Planck function for blackbody radiation at long wavelengths is and $$T_R = T_{BG}\exp(-\alpha(f)Cx) + T_C(1 - \exp(-\alpha(f)Cx))$$
$$= T_C + (T_{BG} - T_C)\exp(-\alpha(f)Cx)$$

Figure 3A:
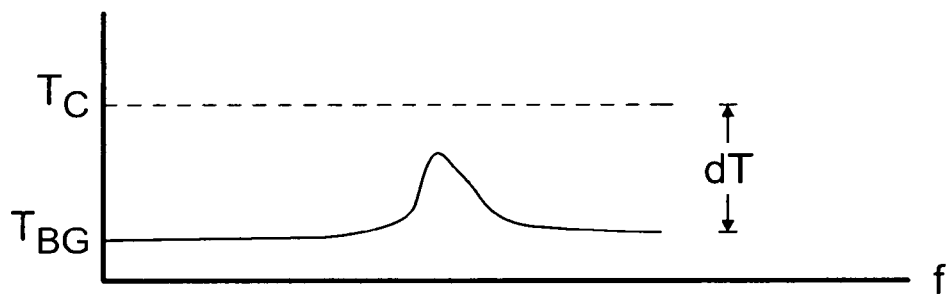
FIGS. 3A-C illustrate various possible plume detection scenarios for use with the present invention, i.e. a plume that emits radiation proportional to its optical depth and dT (FIG. 3A), a plume that absorbs radiation proportional to its optical depth and dT (FIG. 3B), and a plume that is transparent (FIG. 3C)
Figure 3B:
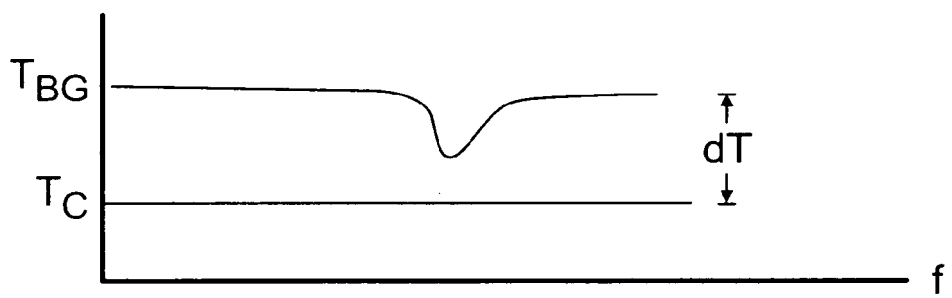
Figure 3C:
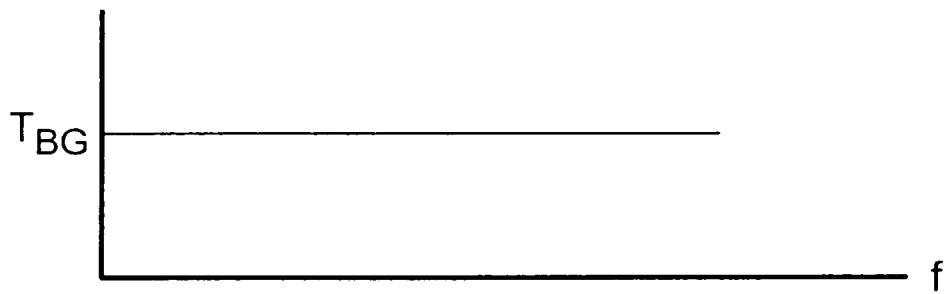

Tbg may be greater than, less than, or equal to T$_c$:
  Case 1: (T$_{bg}$<T$_c$) The plume emits radiation proportional to its optical depth and dT (FIG. 3A).
  Case 2: (T$_{bg}$>T$_c$) The plume absorbs radiation proportional to its optical depth and dT (FIG. 3B).
  Case 3: (T$_{bg}$=T$_c$) The plume is transparent (FIG. 3C).

Figure 4A:
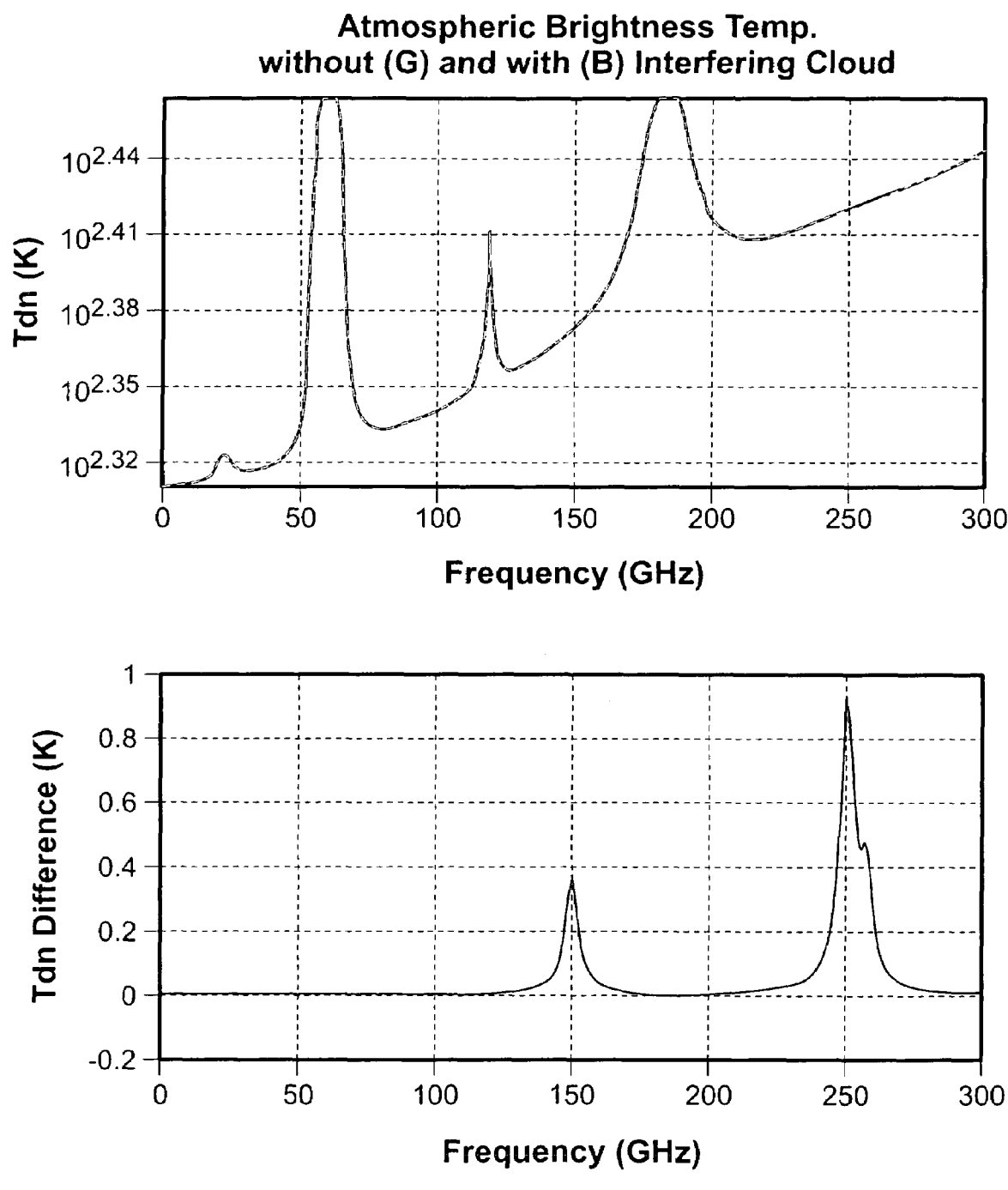
FIGS. 4A-B illustrate the effect of a distance, such as mountain background, on the mmW results.
Figure 4B:
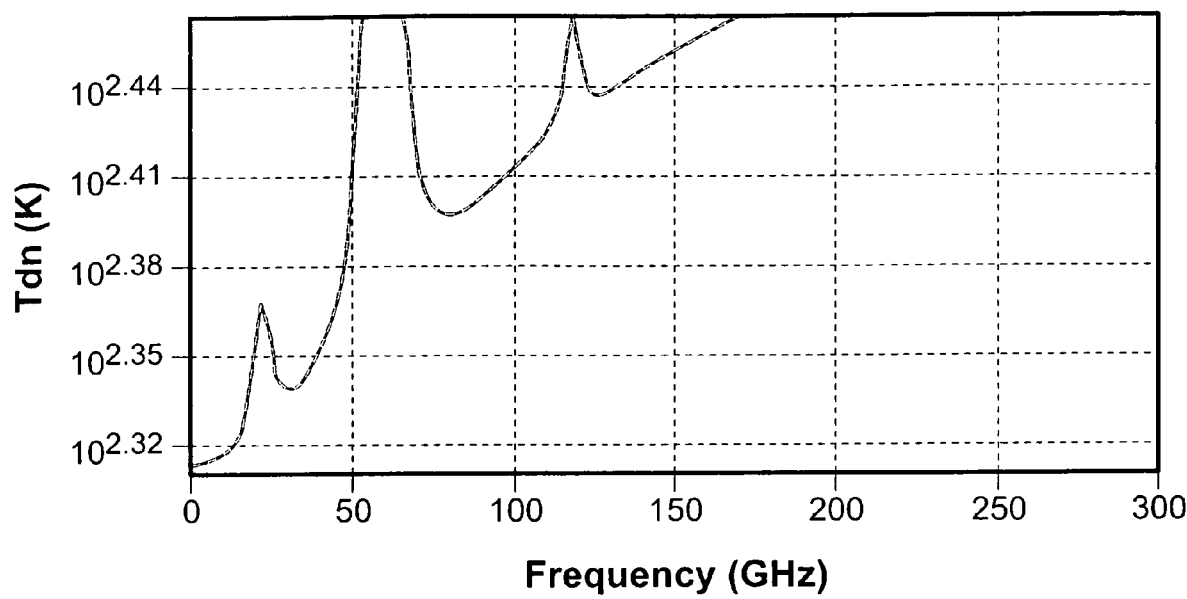
Figure 4B:
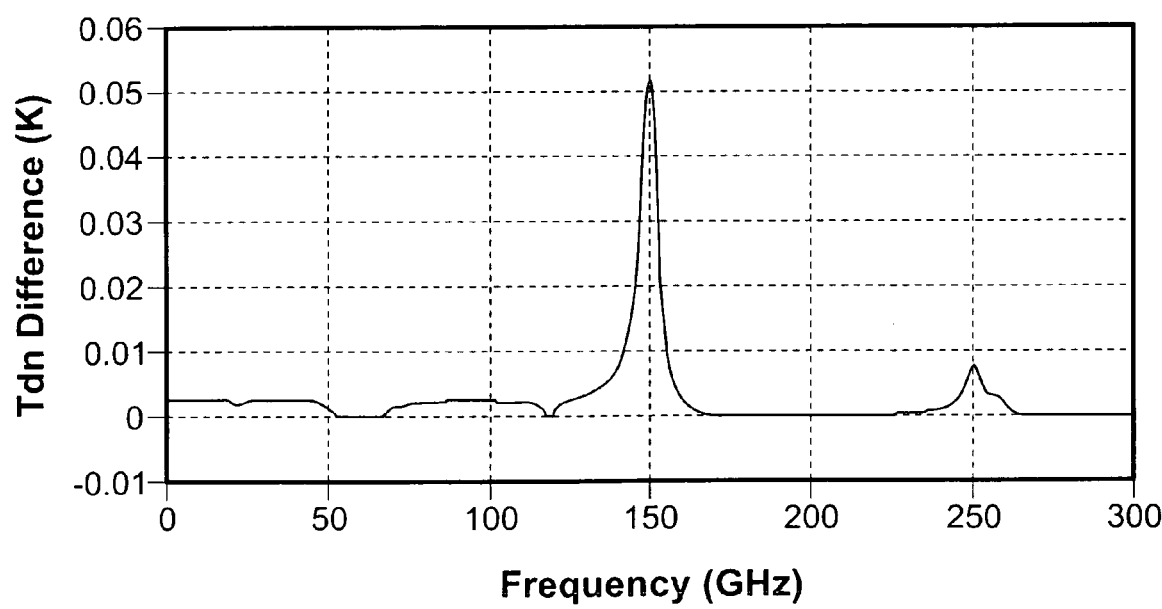

In addition, the distance of the background will have an impact on the mmW results. FIGS. 4A-b illustrates the effect of a distance, such as mountain background, on the mmW results. In FIG. 4A, θ=84.3; R$_c$~1.0 km; R$_{bg}$~2.0 km; H$_c$: 0.1 km; D$_c$: 0.01 km; T$_c$: 288.15 K; ε $_{BG}$~0.7; V%NO: 1. In FIG. 4B, θ=89.4; R$_c$~10.0 km; R$_{bg}$~10.5 km; H$_c$: 0.1 km; D$_c$: 0.01 km; T$_c$: 288.15 K; ε $_{BG}$~0.7; V%NO: 1.

Figure 5A:
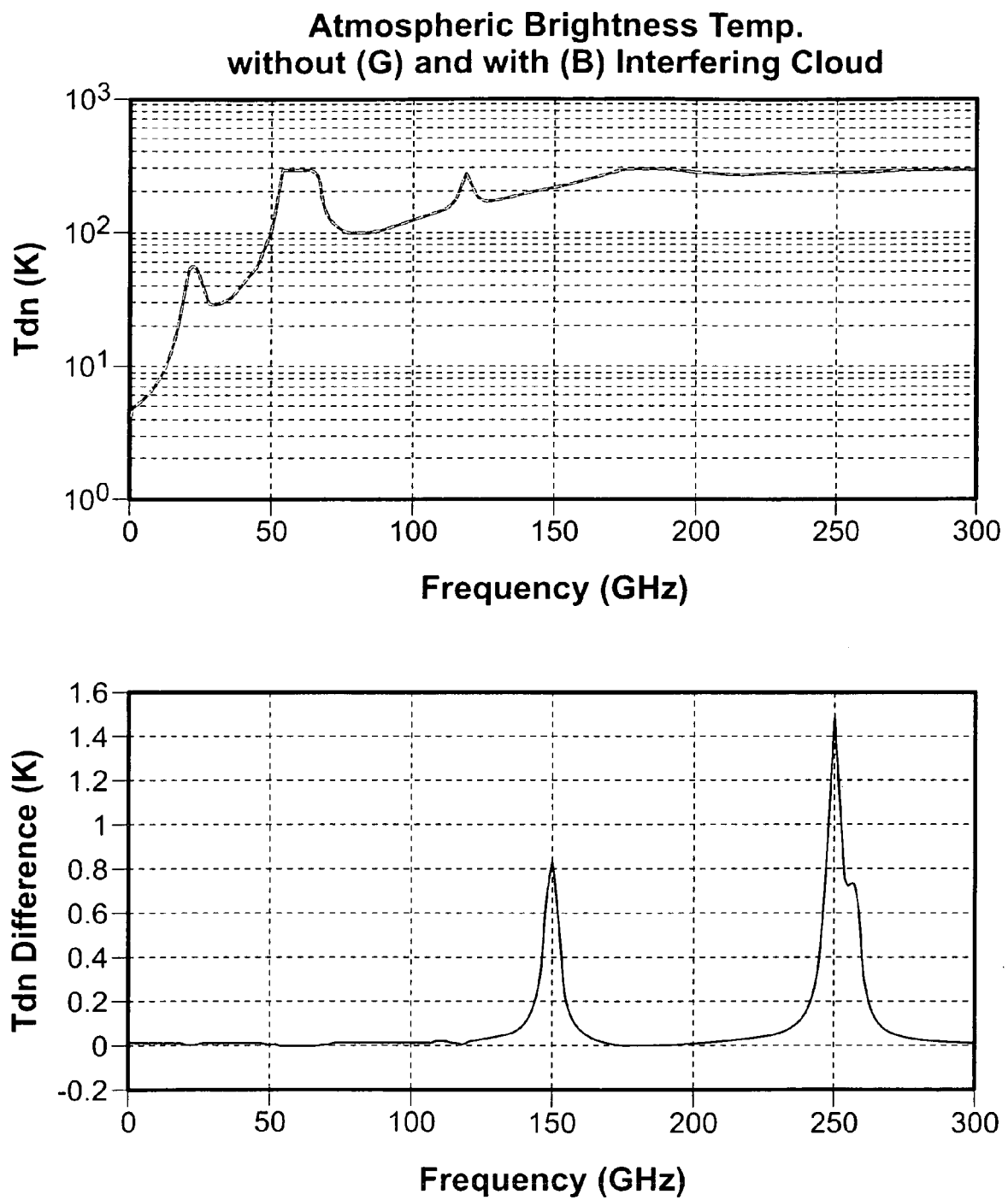
FIGS. 5A-B illustrate the impact of cloud temperature.
Figure 5B:
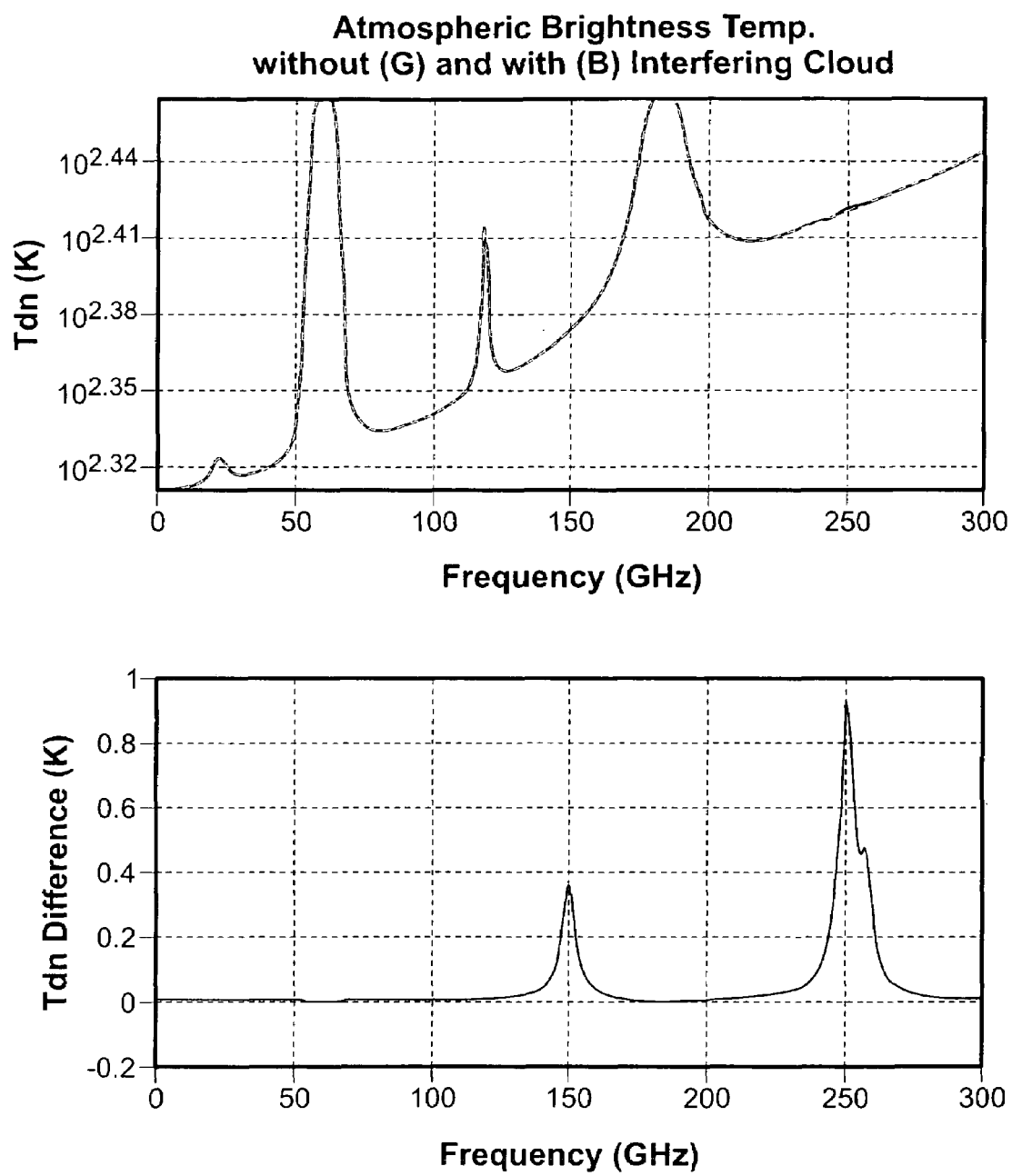

Cloud temperature will also impact the mmW results. FIG. 5A illustrates results where cloud temperature is relatively high (T$_c$: 350 K) and where θ=85; R$_c$~1.15 km; R$_{bg}$~5.7 km; H$_c$: 0.1 km; D$_c$: 0.01 km; V%NO: 1. FIG. 5B illustrates results where cloud temperature is lower relative to FIG. 5A (Tc: 288.15K) and where θ=85; R$_c$~1.15 km; R$_{bg}$~5.7 km; T$_c$: 288.15 K; H$_c$: 0.1 km; D$_c$: 0.01 km; V%NO: 1.

Figure 6A:
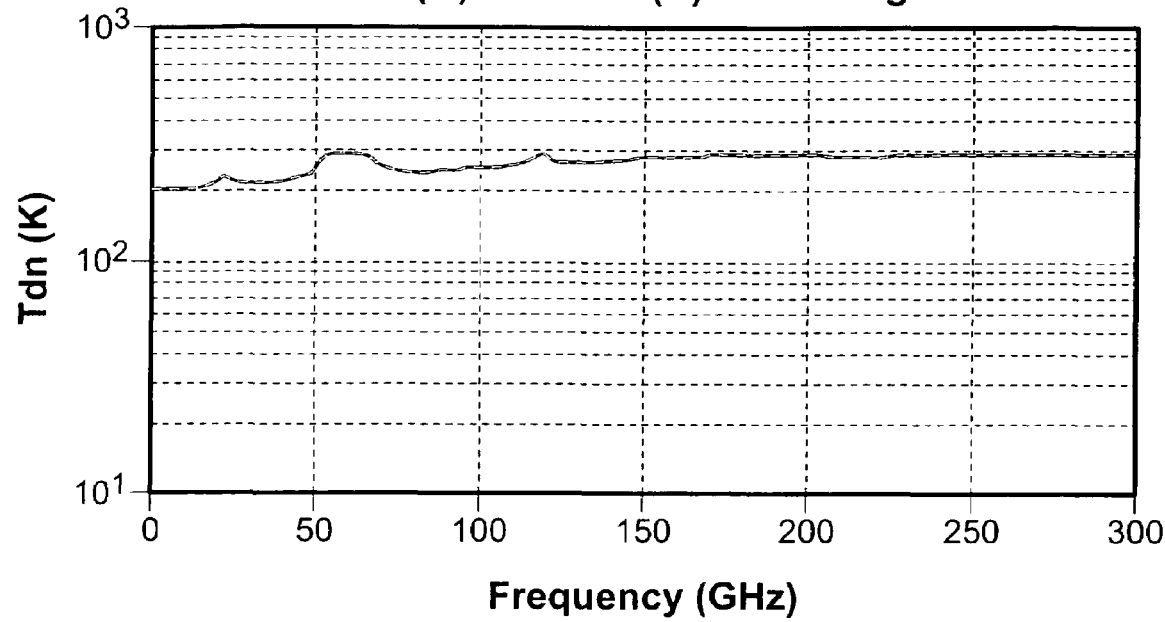
FIGS. 6A-B are graphs showing apparent temperature as a function of frequency and for different volume percent of water vapor in the atmosphere in plume with both the absolute temperature with and without the plume (6A) and the difference temperature (6B)
Figure 6A:
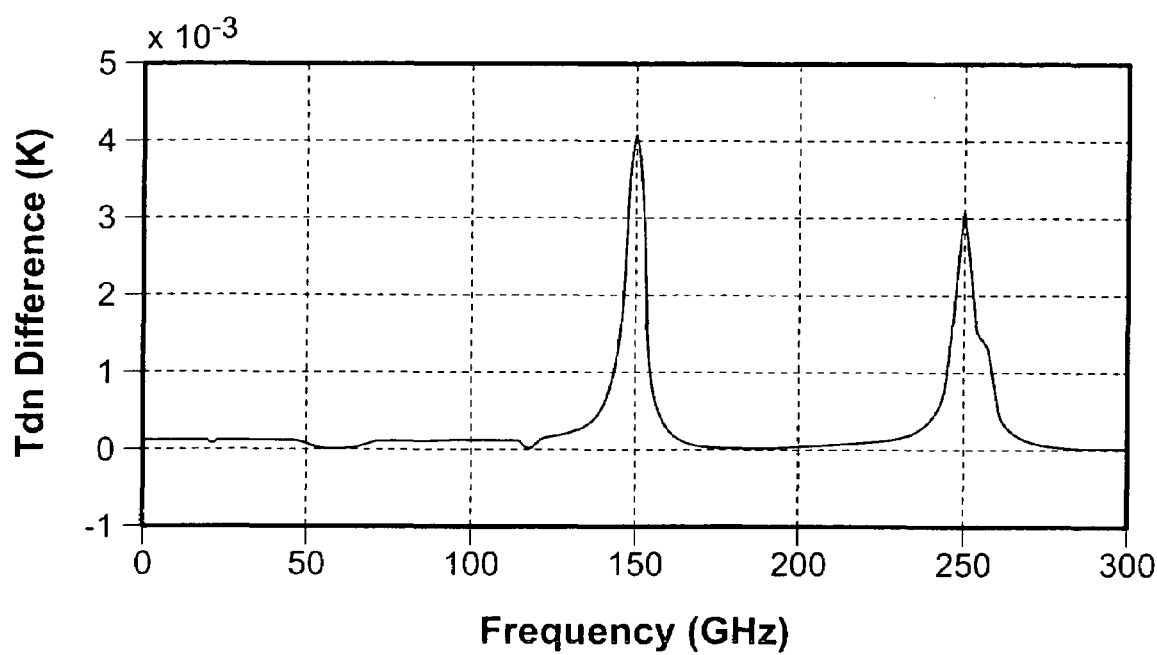
Figure 6B:
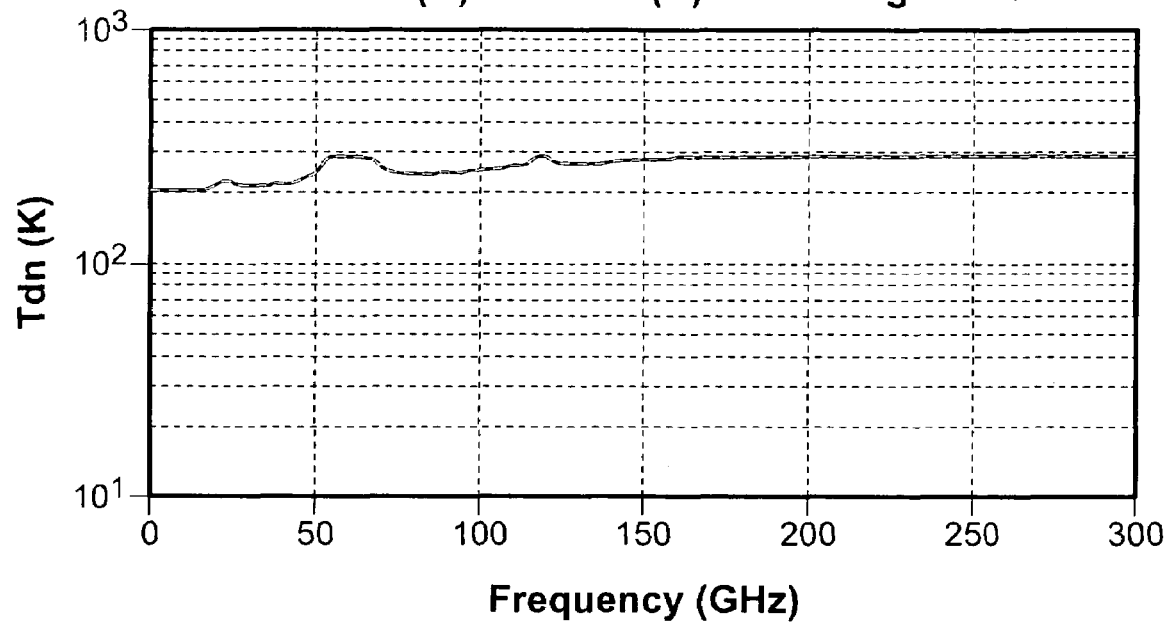
Figure 6B:
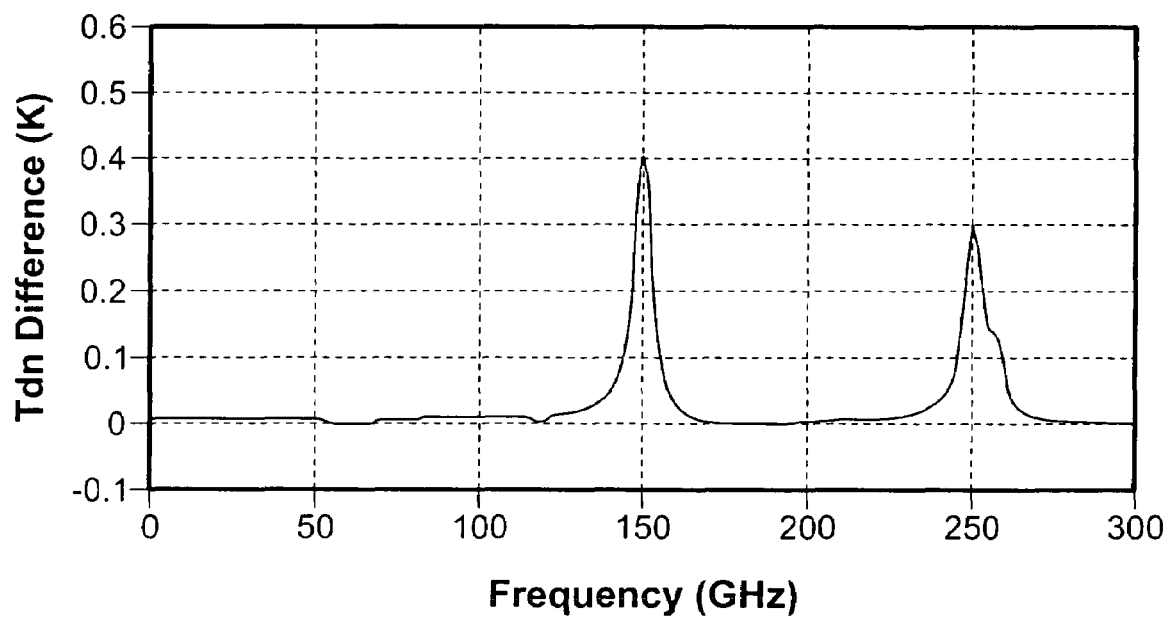

FIG. 6A-B are graphs showing apparent temperature as a function of frequency and for different volume percent of water vapor in the atmosphere in plume with both the absolute temperature with and without the plume (top graph) and the difference temperature (bottom graph). For FIG. 6a V$_\%$=0.02, R$_c$≈5.0 km, R$_{bg}$≈10.0 km and for FIG. 6B, V$_\%$=2.0, R$_c$≈5.0 km, R$_{bg}$≈10.0 km. For all case here h$_c$=0.1 km, d$_c$=0.01 km, T$_c$=288.15 K, ε=0.7 and with 1% by volume of target molecule.

Figure 7:
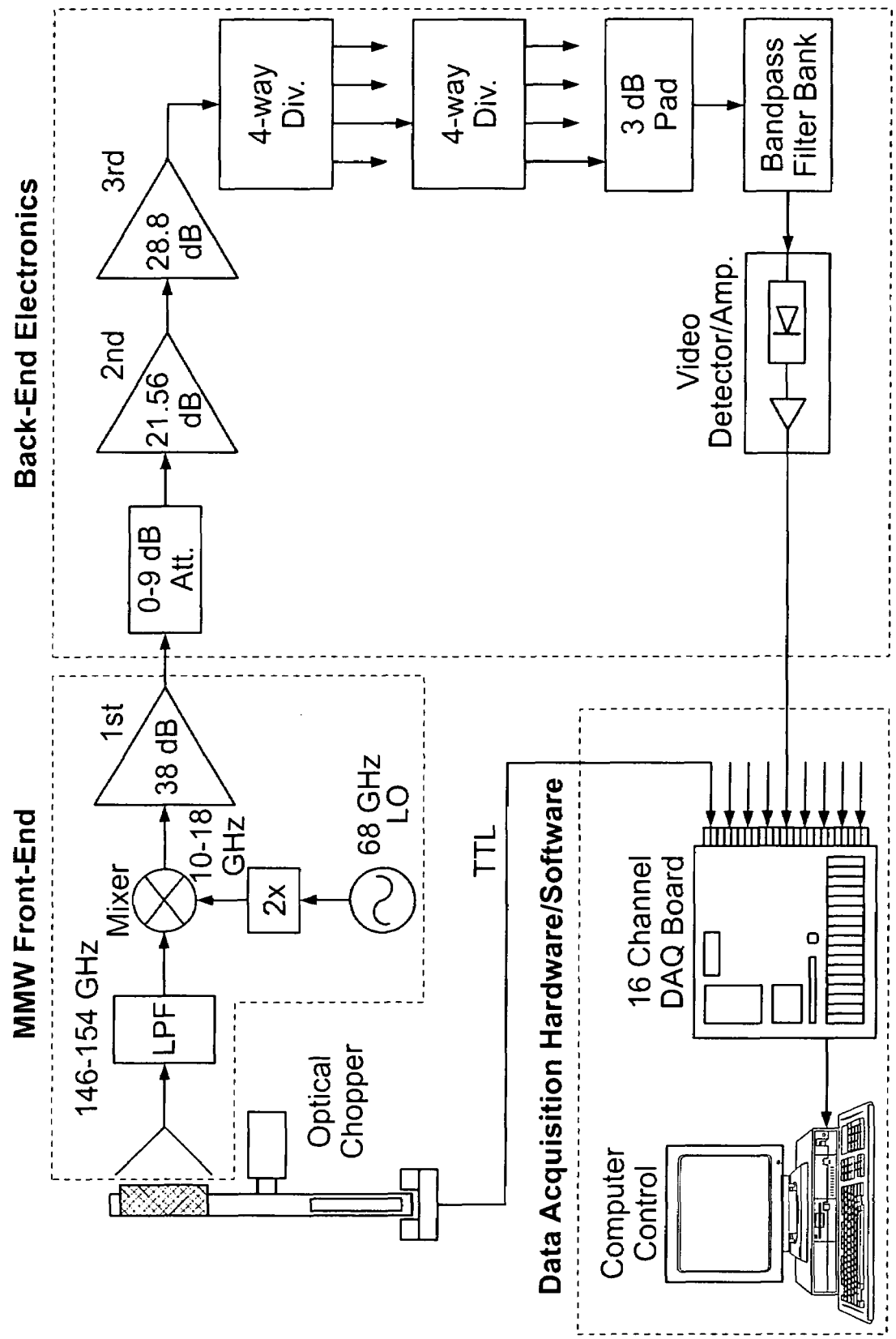
FIG. 7 shows the basic block diagram of one embodiment of the present invention.

One embodiment of the present invention consists of a system 110 comprising a mmW front-end assembly, back-end electronics, and data acquisition hardware and software. FIG. 7 shows the basic block diagram of the system. The system comprises three segments, a front end system 111, a back end system 113, and a data acquisition system 115. The front end system 111 includes a superheterodyne receiver 121 at the front-end which converts the MMW frequencies within the pass band of the low-pass filter down to intermediate frequency (IF) range in microwave X-band which subsequently goes through first-stage amplification 116. The back-end system 113 further amplifies the IF signal by passing it through another two stages of amplification 117, 118. In one embodiment, a two-stage power divider 125 splits the signal into sixteen channels, which then goes trough a bank of sixteen bandpass filters 126 and is subsequently down-converted to video frequency range. In one embodiment, each video amplifier 127 has a Schottky barrier diode detector. In one exemplary embodiment, the front end 111 is thermally isolated and cooled to a constant temperature (~55 deg F.) by a thermoelectric cooler (not shown). To allow the system 110 to operate in Dickie-switched mode, an optical chopper 122 is installed in front of the antenna unit, which provides a trigger signal for separating of the scene and the reference signals. The chopper 122 creates a switching scenario where the sensor switches between a blackbody reference and the target scene. The difference between the signal at each channel is integrated to derive the brightness temperature of the scene. The receiver 121 is periodically calibrated with an absorber at room temperature, heat load at 130 deg C., and a cold load at liquid nitrogen temperature. The outputs of the receiver 121 and the synchronization TTL signal from the optical chopper 122 are all fed to the data acquisition system 115, which in one embodiment comprises a 18-bit data acquisition (DAQ) board 129 for processing by a computer 131.

One aspect of the present invention relates to methods for transforming the data generated by the system described above. In one embodiment, the acquisition and real-time analysis of the data is performed under the LabVIEW™ environment. In another embodiment, algorithms developed under the MATLAB™ may also be used for numerical computation and visualization for post-processing of multichannel spectroscopic data.

Figure 9A:
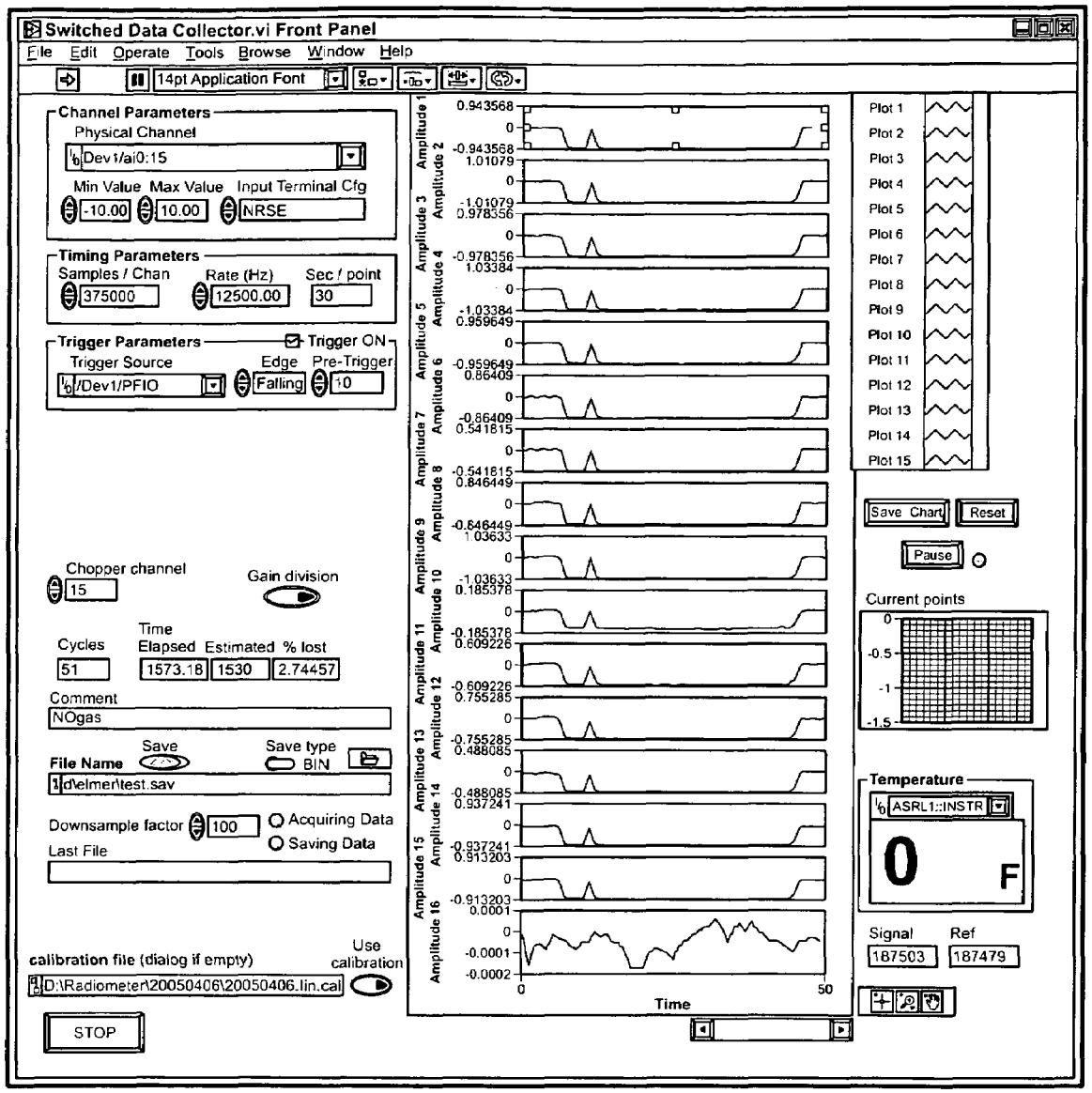
FIGS. 9A-C show the virtual instrument (VI) interface of the acquisition software that was developed using the principles of the present invention under the LabVIEW™ environment to simultaneously (multiplexed) collect data from all sixteen channels of the radiometer.
Figure 9B:
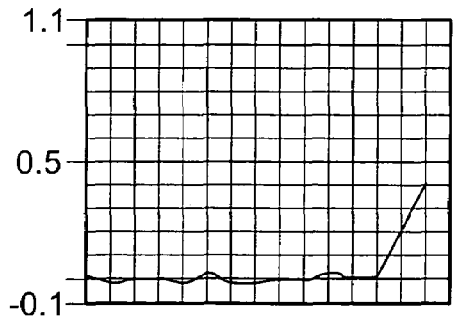
Figure 9C:
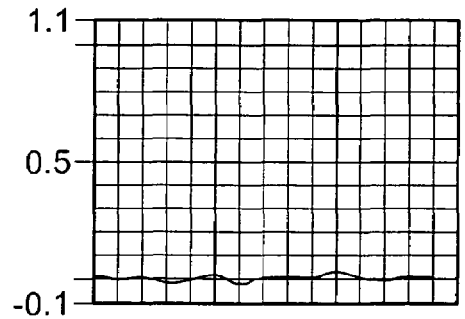

FIGS. 9A-D show the virtual instrument interface of the acquisition software that was developed using the principles of the present invention under the LabVIEW™ environment to simultaneously (multiplexed) collect data from all sixteen channels of the radiometer. FIG. 9a is a screen shot of one embodiment of the present invention from LabVIEW$^T$ user interface implemented for real-time acquisition, analysis, and display of data from a 16-channel radiometer. Text boxes and buttons on this virtual instrument allow adjusting of the test parameters. FIG. 9(B-C) illustrates a close-up of traces of the frequency profile without (top) and with (bottom) the target molecule being present in the gas cell.

The trigger signal from an optical chopper 122 served as the synchronization trigger for emulating the Dicke-switching mode. In one embodiment, the primary functions of the software include simultaneous acquisition and recording of raw data, real-time reference subtraction, instantaneous display of spectral lines across frequency channels, options to save the original and differential traces, down-sampling, dynamic calibration, creating of event markers for post analysis, monitoring and saving of temperature data from the cooling system. Although real-time processing and display of the spectral data under LabVIEW™ was adequate for detection of radiometric temperature variations for strongly emitting/absorbing molecules, this pre-processing of data in this manner does not allow for detection sensitivities in the milli-Kelvin level that was needed to detect weakly emitting target molecules of interest. Therefore, in one embodiment, additional post-processing of data is performed to reach the necessary level of sensitivity.

Figures 14A, 14B:
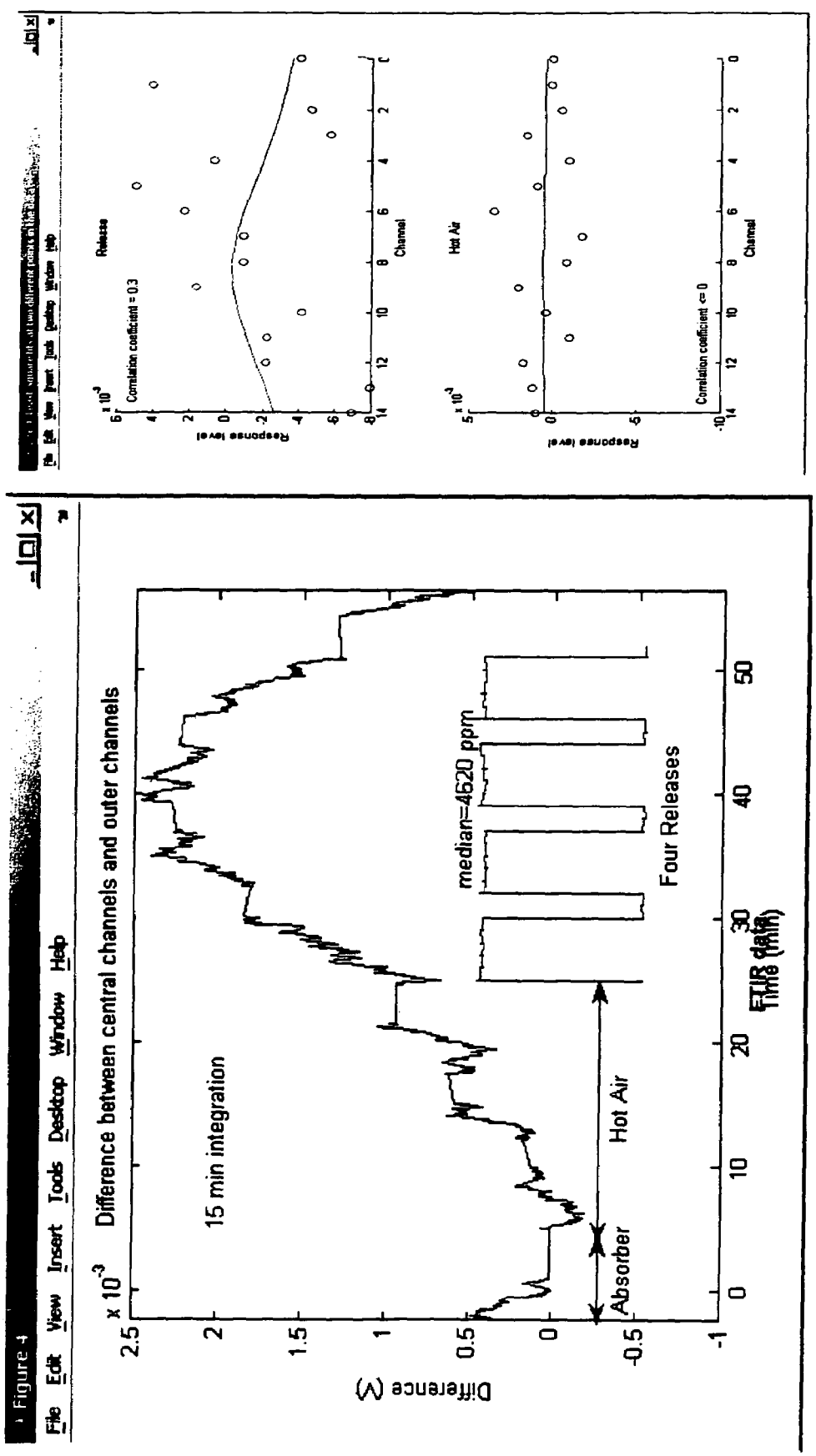
FIG. 14A-B illustrate detection of nitric oxide plume from 600 m using the embodiment of FIG. 11.

A series of algorithms were implemented in MATLAB™ programming language for post processing of the radiometric data. In one embodiment operations are simplified by using scripts integrated into a graphical user interface, 150 (FIG. 9A) (GUI), whose algorithmic steps are shown in FIGS. 12. In an exemplary embodiment, radiometric data may be processed and displayed by the GUI in various formats including time domain trace and image format and frequency domain profile (FIG. 14). In reference to FIG. 14, to help improve visualization of trends in the frequency profile, a least-square based routine for fitting of an arbitrary order polynomial to the data was implemented. In one embodiment, the main post-processing stages of the data are listed as follows:
1. Amplitude normalization
2. Frequency domain scene subtraction
3. Time domain integration
4. Time domain baseline subtraction
5. Channel stacking In the first stage the amplitude of all channels are independently normalized to adjust for gain variations among the channels by using calibrated loads. The scaling factors are typically calculated based on a hot and a cold load. The scaling routine also allows one to compensate for system drifts by adjusting slow baseline fluctuations through an arbitrarily selected polynomial fit. Because the system 110 is intended for the detection of a target molecule, effect of atmospheric and system fluctuations should therefore be minimized. Compensation for scene (path) is done by subtracting the frequency profile of the scene at the beginning of the measurement. Next, all data traces are integrated by using a moving average filter. The filter parameters are selected based on the integration time necessary. The peak absorption by the target molecule occurs near the center of the radiometer bandwidth. Fluctuations of the scene, however, are expected to be equally contributing to all channels within the bandwidth. Therefore, to compensate for atmospheric fluctuations over extended periods of time, the entire trace from an end channel is finally subtracted from all other channels. Because the system 110 temperature resolution is inversely proportional to the square root of the operating bandwidth a routine was also implemented to emulate bandwidth improvement. This process is also integrated into the GUI and allows one to arbitrarily stack the frequency channels with maximum signal strength and subtract the end channels at which the response is significantly lower (FIG. 14).

In addition to the main processing routines described above, in exemplary embodiments additional data analysis schemes are also implemented to help better visualize the trends in radiometric data. For example, such schemes may include time-domain digital filtering and least-square fitting of known line shape functions to frequency cross sections of the temporal data.

Figure 10:
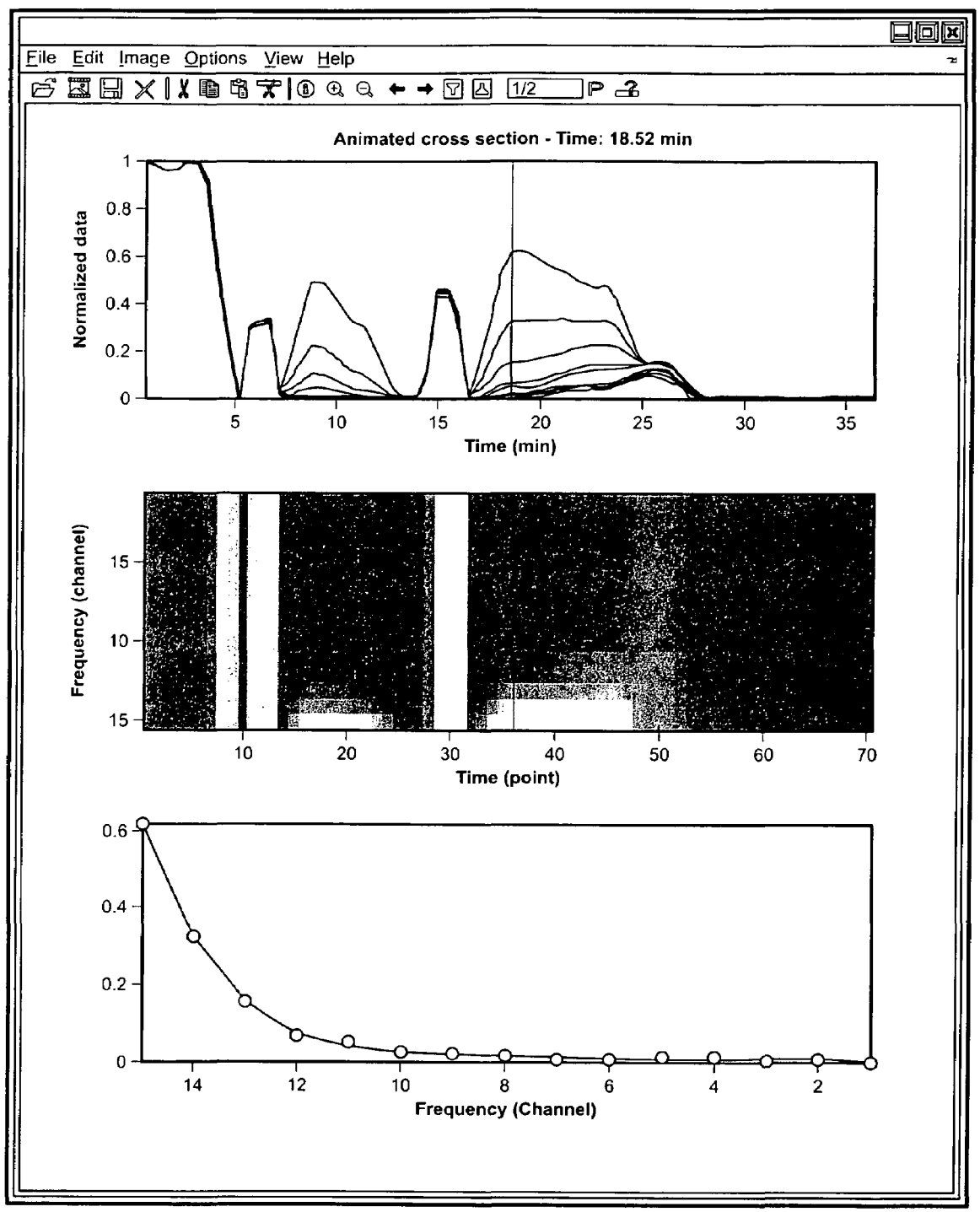
FIG. 10 illustrate the spectral data from one embodiment of the present invention as displayed on graphical user interface, the upper portion illustrates the signal trace for a sequence of blackbody, hand, CH$_3$CN, vacuum, and CH$_3$CN (40 Torr), the middle portion a 2-D image of signal intensity across fifteen frequency channels, and the lower portion the spectra of CH$_3$CN at 6 Torr and 40 Torr.
Figure 11:
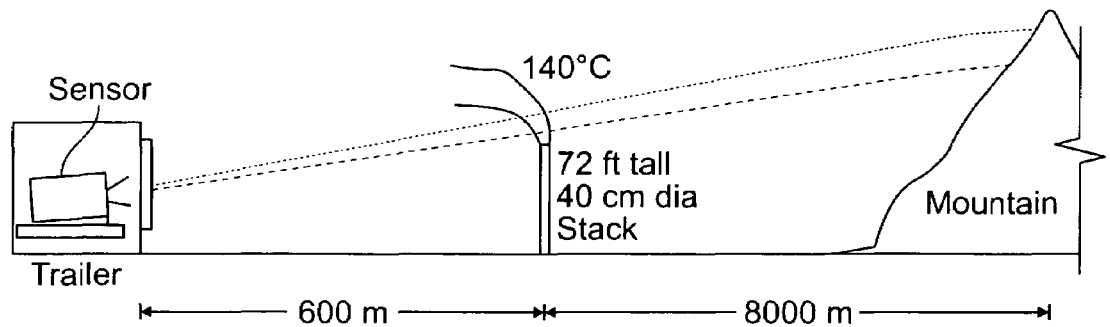
FIG. 11 is an illustration of a test setup for one embodiment of the present invention.

FIG. 10 is a screen shot from MATLAB™-based graphical user interface that was implemented for post-processing and display of multi-channel radiometric data. Graphics show the time trace (top), image (middle), and frequency cross section (bottom) of the post-processed data for a strongly emitting molecule. The measurements were carried out in the laboratory by using a target molecule with known spectral lines.

The raw data generated by one embodiment of the invention contains a relatively high level of noise. Therefore, in an exemplary embodiment, Dicke-switched integrated data is used. FIG. 14 illustrates graphically the output of the raw data in comparison to the integrated data. In one embodiment, the difference signal between reference and scene integrated in LabVIEW™ software; allows long integration times up to several minutes.

The present invention may be used with a plethora of frequency combinations and bandwidths. In one embodiment, 16 frequency channels are used to cover 146 GHz to 154 GHz with 500 MHz bandwidth.

One skilled in the art will appreciate the myriad of applications for the present invention, including for defense and intelligence applications. In one embodiment, the present invention may be used to provide an indication of the type of contraband product being manufactured by a rogue nation or group; it may be covertly gleaned from remote measurements of the effluent chemicals of their processing operations. In another embodiment, the present invention may be used in dealing with environmental compliance and arms control treaty verification. In another embodiment, the present invention may be used to detect hydrocarbon leaks, such as in oil refinery process lines, assuring safety and savings in fuel. Various embodiments of the present invention can be employed in a wide range of biomedical and biometric applications. In an exemplary embodiment, the present invention relates to non-contact sensing of subcutaneous temperature of human organs (e.g., breast tumor) for medical diagnostics and imaging of subjects for concealed weapons and explosives.

Illustrations of the Present Invention

Figure 8:
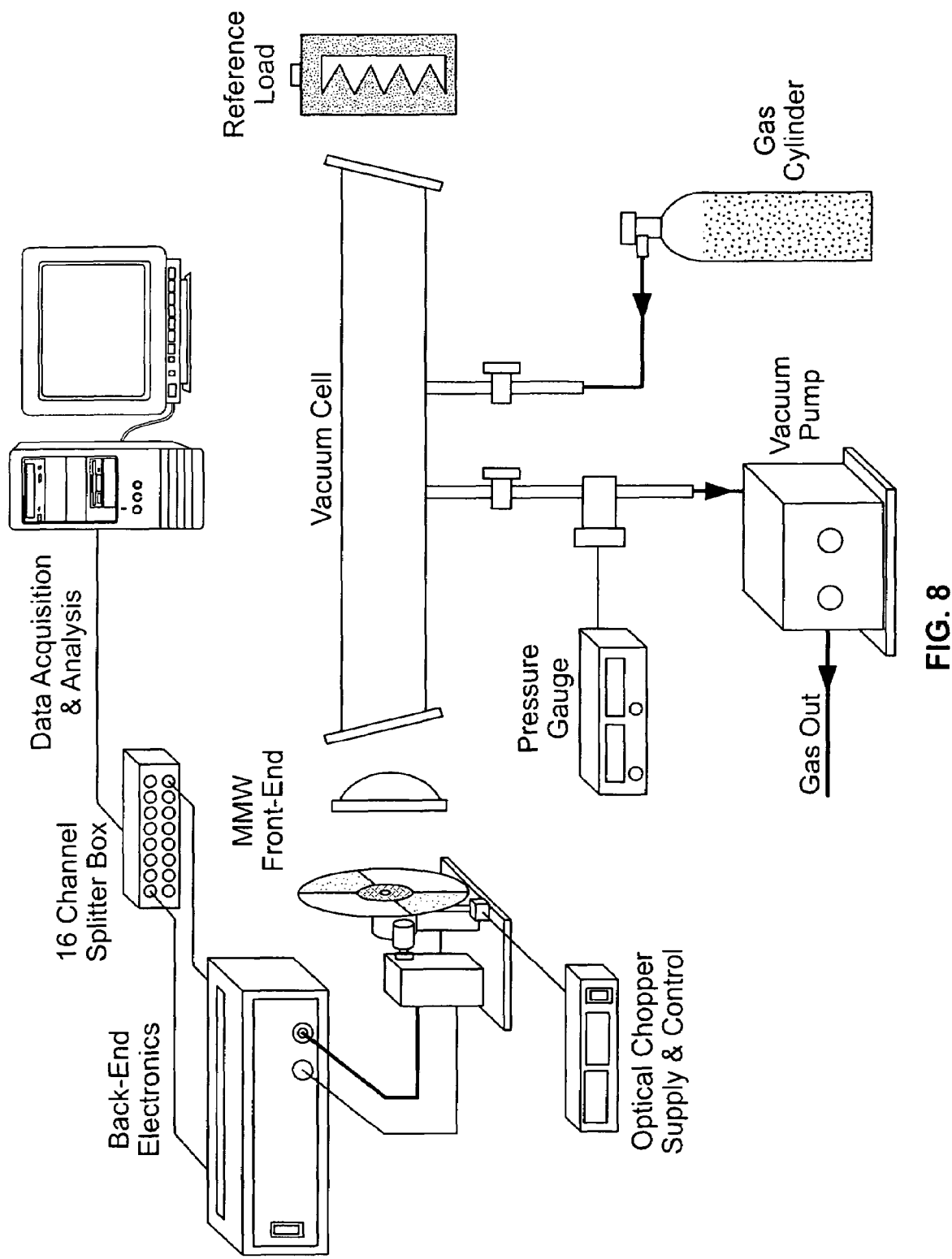
FIG. 8 shows one embodiment of the present invention for testing in a laboratory setting.

A passive millimeter-wave sensor for remote detection of chemical spectra between 146 GHz and 154 Ghz was field tested at the Nevada test site, successfully detecting the target chemical from a hot stack 600 m away. A sequence of four 5-min releases of NO at 4600 ppm with 2 minute breaks in between releases for calibration and 20 min of hot air for comparison (FIG. 14). A ten minute release of NO at 2852 ppm with hot air was also performed. FIG. 8 is an illustration of one embodiment of the laboratory apparatus for passive measurement of emission spectra of gases at millimeter wavelengths.

For the proof of principle of passive mmW spectroscopy, several experiments were conducted by using chemicals with known absorption lines. The laboratory set up for the measurement of emission spectra at millimeter wavelengths is shown in FIG. 8. The laboratory setup was as described for the system 110 of FIG. 7, using a front end system 111, a back end system 113 and a data acquisition system 115. In addition, the laboratory setup of FIG. 8 utilized a sample setup 140. The sample setup 140 includes a reference load 141 in communication with a vacuum cell 142. The vacuum cell 142 is operatively connected to a gas cylinder 145, a vacuum pump 144, and a pressure gauge 143. The gas was pumped into a vacuum cell and the emission spectra due to thermal contrast between the gas at ambient temperature and the cold load background was measured by the radiometer. The frequency spectrum centered around 147 GHz is shown for $CH_3CN$ in FIG. 10. The measurement was made with a 30 second integration time and over a ~30 minute time span. The radiometer response for the hot load (time interval between 0 and 5 min.), hand (time intervals centered at ~7 min. and ~15 min.), and the gas (centered at ~10 min. and ~20 min.) are clearly visible in both the linear trace and the image display of the same data. The peak emission spectra located at ~18 min. is shown in the bottom plot. A polynomial fit to the measured data points is also shown on the same plot.

FIG. 10 contains graphs of laboratory measurement results for $CH_3CN$ gas at various pressures. FIG. 10, the bottom graph depicts the frequency spectra at a given instant in time that is marked by the vertical line in the top graph of FIG. 10.

Figure 12A:
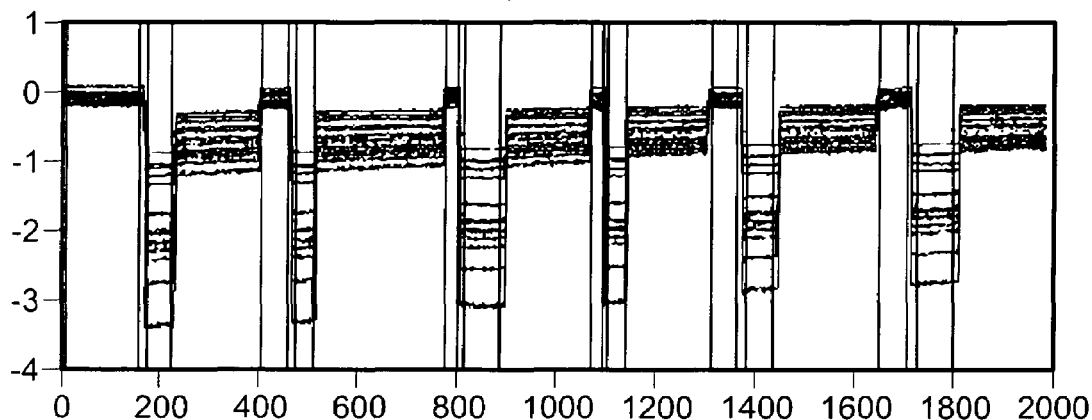
FIGS. 12A-D graphically illustrates original data (FIG. 12A) and data after gain calibration (FIG. 12B), frequency baseline subtraction (FIG. 12C), temporal baseline subtraction (FIG. 12D)
Figure 12B:
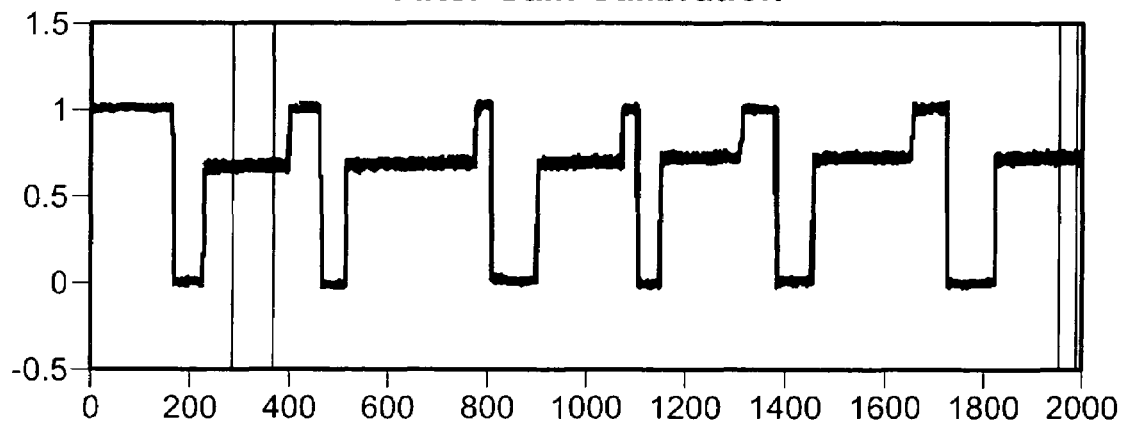
Figure 12C:
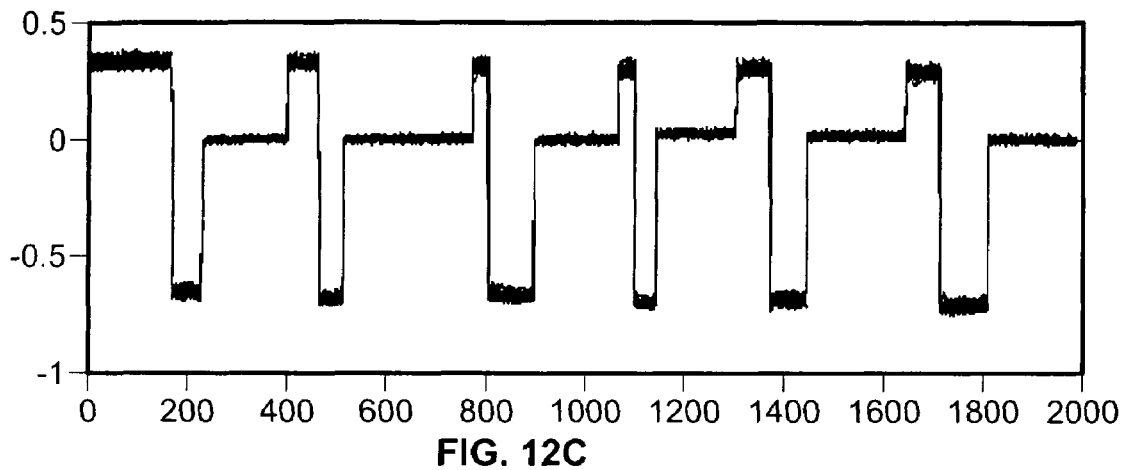
Figure 12D:
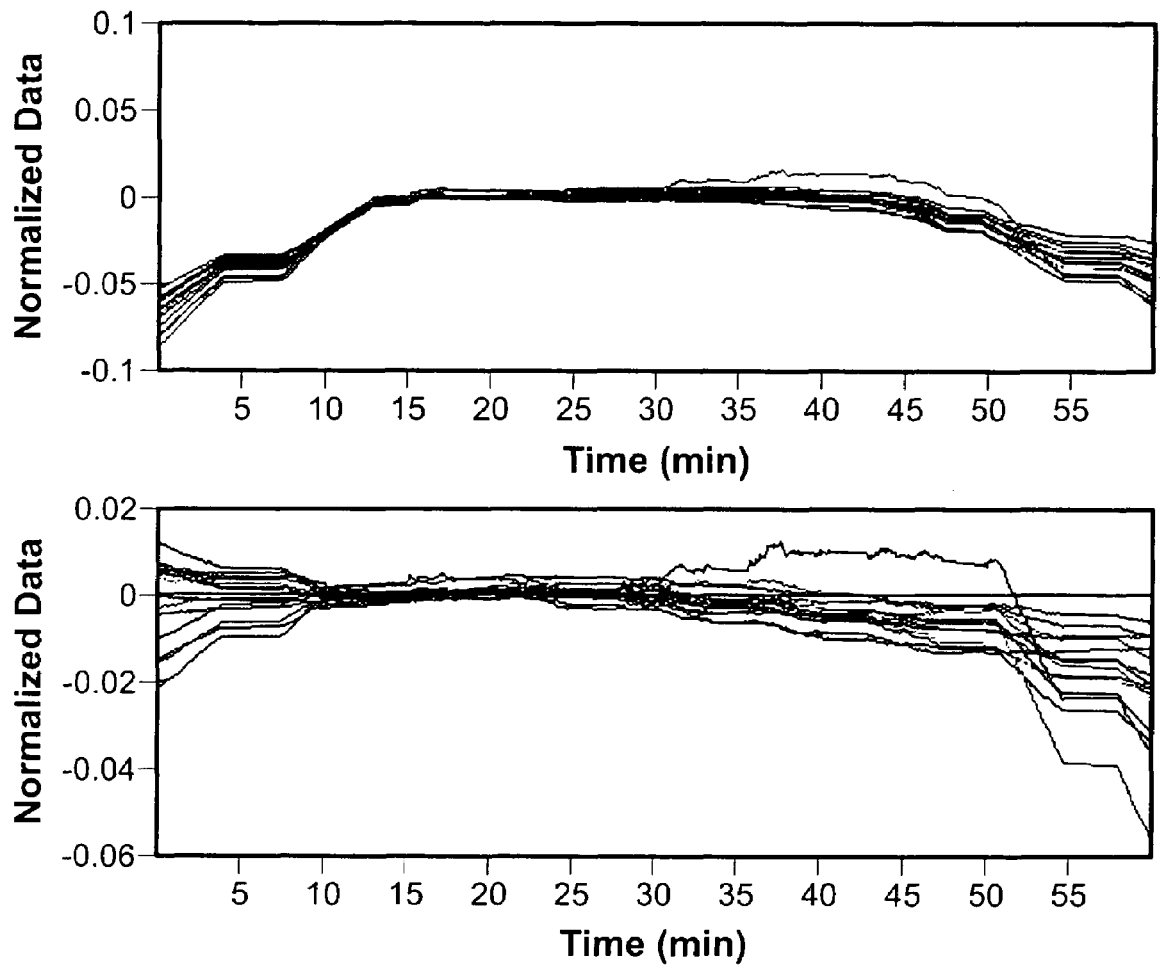
Figure 13:
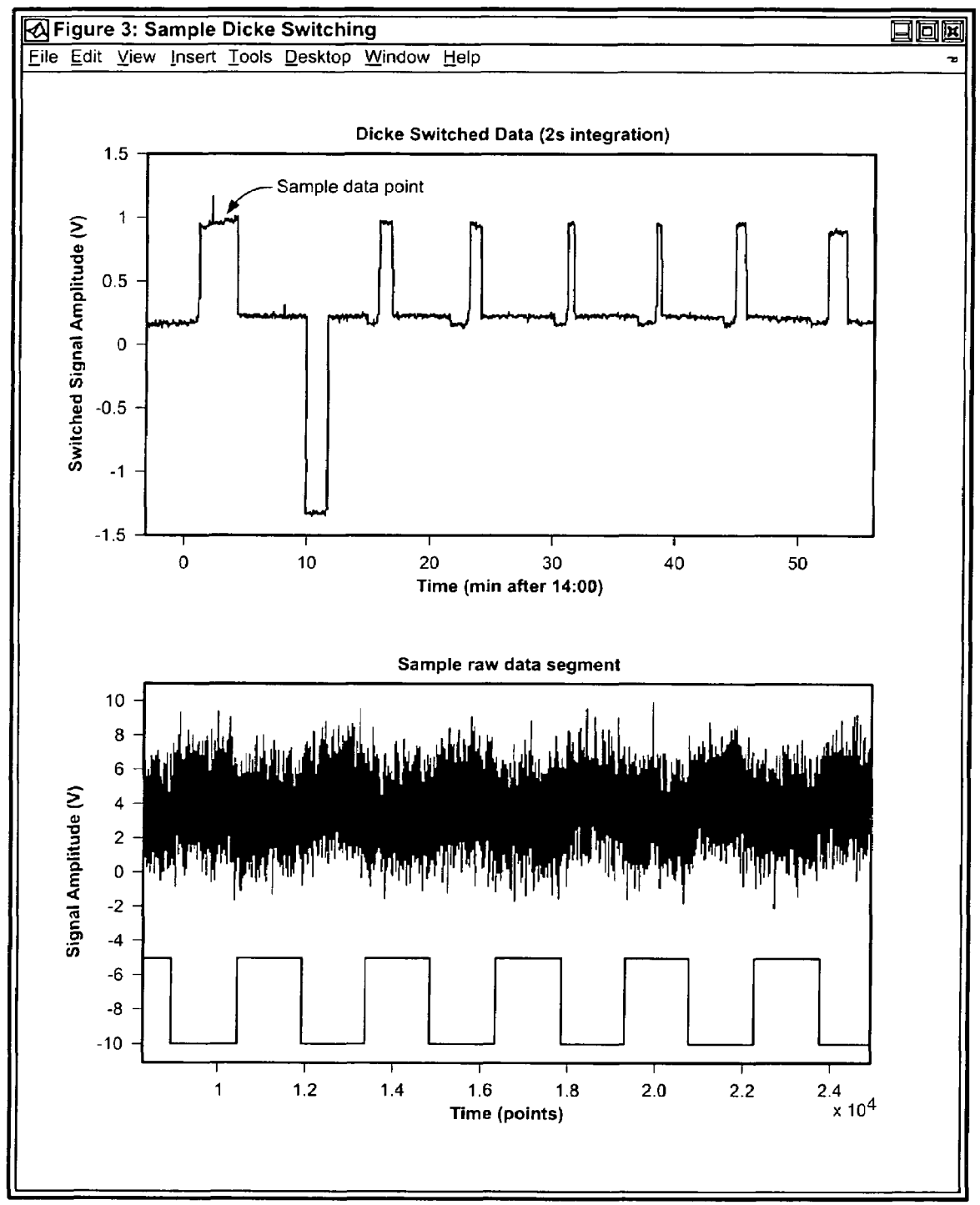
FIG. 13 illustrates a graphical representation of raw millimeter wave data (bottom portion) and the same data which has been Dicke switched with a two second integration (top portion)

The original data received was then subjected to a number of signal processing steps. (FIG. 12a) First the gain was calibrated to ensure that all of the channels to response to the same signal height between two calibration loads. (FIG. 12b) Next, the frequency baseline was subtracted to eliminate the baseline across the frequency channels inherent among the receiver channels. (FIG. 12c) Then, the temporal baseline is subtracted from the data to eliminate any fluctuation associated with temporal changes, resulting in only the signal variation across the channels. (FIG. 12d)

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. An apparatus for remote detection of chemicals, comprising:
   front end unit comprising a receiver, and an optical chopper;
   a back end unit comprising an amplifier; and
   a data acquisition and analysis module;
   wherein the front end unit detects millimeter waves and separates millimeter wave associated with a background from the millimeter wave associated with a foreground using the optical chopper, the receiver transmitting a signal representative of the detected millimeter waves for pre-processing and amplification by the back end unit which transmits the signal to the data acquisition module for post-processing and detection of the chemicals.

2. The apparatus of claim 1 wherein post processing is performed by at least one component selected from the group consisting of a component for amplitude normalization, frequency domain scene subtraction, time domain integration, time domain baseline subtraction, channel stacking, and combinations thereof.

3. The apparatus of claim 1 wherein the receiver comprises a superheterodyne receiver which converts the millimeter waves to intermediary frequency range waves.

4. The apparatus of claim 3 wherein the back end unit includes a component which amplifies the intermediary frequency waves and splits the signal into a plurality of channels.

5. The apparatus of claim 4 wherein the signal includes a component for separation into four channels of data.

6. The apparatus of claim 5 wherein each of the four split channels of data is further split into four channels forming sixteen channels of data.

7. The apparatus of claim 1 wherein the receiver includes a component which functions in a Dickie-switched mode.

8. The apparatus of claim 1 wherein the data acquisition and analysis module comprises a computer system.

9. The apparatus of claim 8 wherein the computer system comprises computer program code for graphical display of a millimeter wave profile.

* * * * *